(12) United States Patent
Elsässer et al.

(10) Patent No.: US 10,039,512 B2
(45) Date of Patent: Aug. 7, 2018

(54) IMAGE QUALITY IN COMPUTED TOMOGRAPHY USING REDUNDANT INFORMATION IN PRODUCTION DATA SETS

(71) Applicants: Thilo Elsässer, Buckenhof (DE); Robert Frysch, Magdeburg (DE); Georg Rose, Magdeburg (DE)

(72) Inventors: Thilo Elsässer, Buckenhof (DE); Robert Frysch, Magdeburg (DE); Georg Rose, Magdeburg (DE)

(73) Assignee: Siemens Healthcare GmbH, Erlangen (DE)

( * ) Notice: Subject to any disclaimer, the term of this patent is extended or adjusted under 35 U.S.C. 154(b) by 10 days.

(21) Appl. No.: 15/275,773

(22) Filed: Sep. 26, 2016

(65) Prior Publication Data

US 2017/0086767 A1      Mar. 30, 2017

(30) Foreign Application Priority Data

Sep. 28, 2015   (DE) .................. 10 2015 218 596

(51) Int. Cl.
    *A61B 6/00* (2006.01)
    *G01N 23/046* (2018.01)
    *A61B 6/03* (2006.01)

(52) U.S. Cl.
    CPC ............ *A61B 6/5205* (2013.01); *A61B 6/032* (2013.01); *A61B 6/5264* (2013.01); *G01N 23/046* (2013.01); *G01N 2223/42* (2013.01); *G01N 2223/612* (2013.01)

(58) Field of Classification Search
    CPC ..... A61B 6/5205; A61B 6/5264; A61B 6/032; G01N 23/046; G01N 2223/612; G01N 2223/42
    See application file for complete search history.

(56) References Cited

U.S. PATENT DOCUMENTS

| 2005/0053188 A1* | 3/2005 | Gohno | A61B 6/032 378/15 |
| 2006/0222145 A1* | 10/2006 | Motomura | A61B 6/032 378/20 |

(Continued)

FOREIGN PATENT DOCUMENTS

| EP | 2490180 A1 | 8/2012 |
| WO | WO2014108237 A1 | 7/2014 |

OTHER PUBLICATIONS

Debbeler C. et al., "A New CT Rawdata Redundancy Measure applied to Automated Misalignment Correction," The 12th International Meeting on Fully Three-Dimensional Image Reconstruction in Radiology and Nuclear Medicine, pp. 264-267, XP055101537, 2013.

(Continued)

*Primary Examiner* — Ming Hon
(74) *Attorney, Agent, or Firm* — Lempia Summerfield Katz LLC

(57) ABSTRACT

A method is provided for detecting a movement of a body between acquisition times of at least two acquisition data sets, wherein, for virtual sectional planes of the body, a first intermediate function value of attenuation values of all the body elements lying in the sectional plane is determined based on a first acquisition data set, and a second intermediate function value of the attenuation values is determined based on a second acquisition data set. For each sectional plane, a difference value is determined from the intermediate function values. A total error value for the two acquisition data sets is calculated by combining the difference values of all the sectional planes. The virtual sectional planes have a common line of intersection, and for the particular acquisition time, the difference between pairs of the sectional lines is at least one pixel.

14 Claims, 3 Drawing Sheets

(56) References Cited

U.S. PATENT DOCUMENTS

| | | | |
|---|---|---|---|
| 2009/0110256 A1* | 4/2009 | Thielemans | A61B 6/032 382/131 |
| 2010/0172561 A1* | 7/2010 | Ota | G01N 23/046 382/131 |
| 2010/0202675 A1* | 8/2010 | Takanaka | A61B 6/032 382/130 |
| 2012/0308105 A1* | 12/2012 | Stancanello | A61B 6/025 382/131 |
| 2014/0161227 A1* | 6/2014 | Flohr | A61B 6/482 378/62 |

OTHER PUBLICATIONS

German office Action for related German Application No. 10 2015 218 596.6 dated May 13, 2016, with English Translation.

Grangeat; P.: "Analyse d'un système d'imagerie 3D par reconstruction à partir de radiographies X en géométrie conique", Thèse de doctorat, Ecole Nationale Supérieure des Télécommunications, with English Abstract, Jun. 1987.

Kyriakou Y. et al.: "Simultaneous misalignment correction for approximate circular cone-beam computed tomography", in: Physics in Medicine and Biology, vol. 53, 2008, pp. 6267-6289, doi:10.1088/0031-9155/53/22/001, 2008.

Maes F, Collignon A, Vandermeulen D, Marchal G, Suetens P. , "Multimodality image registration by maximization of mutual information," IEEE Trans.Med.Imaging Apr. 16(2), 187-198 (1997).

Yu Hengyong et al: "Data Consistency Based Rigid Motion Artifact Reduction in Fan-Beam CT"; IEEE Transactions on Medical Imaging vol. 26 No. 2; pp. 249-260, Feb. 2007.

\* cited by examiner

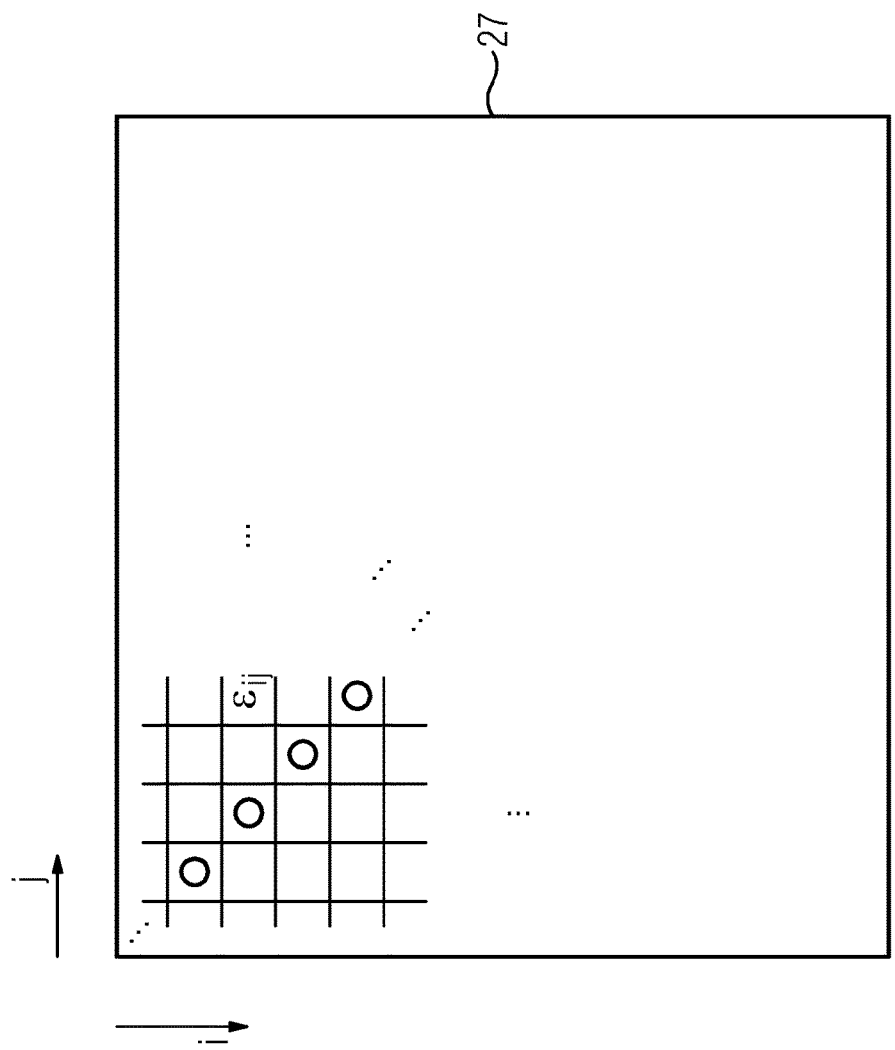

IMAGE QUALITY IN COMPUTED TOMOGRAPHY USING REDUNDANT INFORMATION IN PRODUCTION DATA SETS

This application claims the benefit of DE 10 2015 218 596.6, filed on Sep. 28, 2015, which is hereby incorporated by reference in its entirety.

TECHNICAL FIELD

The embodiments relate to a method for detecting a movement of at least one part of a body that the body has performed between two acquisition times of acquisition data sets in a tomography machine. The movement is detected from the acquisition data sets themselves. A tomography machine that may be used to perform the method is also disclosed.

BACKGROUND

A tomography machine may be used to pass a radiation beam through a body, (e.g., the body of a patient), from different projection angles. The radiation beam hits a detector surface of the tomography machine, where individual pixel sensors, one for each picture element or pixel of the detector surface, detect the radiation intensity. The pixel values of a projection or acquisition are brought together in an acquisition data set. An acquisition data set refers to a data set containing pixel values of pixels of a detector surface of a tomography machine, wherein each pixel value characterizes the effect of attenuation values of body elements of the body on a projection beam that has passed through the body elements successively at a defined acquisition time and has then hit the pixel of the detector surface.

A graphical 3D model of the body may be reconstructed from the acquisition data sets that were obtained from different projection angles. The 3D model may be obtained, for example, using the known algorithm of filtered back projection. In order for this 3D reconstruction to produce a sharp or clear image of body elements of the body, so for instance of internal organs, it is necessary that the position of the body does not change, (e.g., the body remains stationary), in order that the pixel values from different acquisition data sets may be assigned correctly to the image values of the object. Should the body move, then a correct assignment may still be made if the movement is known precisely (e.g., by an additional tracking system). If this information is not available, an image of the body regions in the 3D model is obtained that is blurred or impaired by overlaid stripes (e.g., originating from edges). The generic term "motion artifacts" is used here.

A method for detecting a movement of a body is known from EP 2 490 180 A1, which method uses two acquisition data sets as the basis for calculating in each case a derivative of a planar integral, which derivative is also referred to as an intermediate function. The planar integral constitutes the 3D Radon transform. The intermediate function value characterizes for a virtual sectional plane of the body, the total of all the attenuation values of the body elements of the body that are located in this sectional plane. The intermediate function value may be determined here on the basis of the first acquisition data set and also independently thereof on the basis of the second acquisition data set. If the body has moved between the acquisition times of the two projections, then the two intermediate function values will differ.

A method for correcting misalignment for imaging techniques is known from WO 2014/108237 A1. This method likewise uses the intermediate function to determine a difference between two acquisition data sets. This publication denotes the intermediate function by the function $g_3$. In order to determine the geometric misalignment (caused by, e.g., incorrect calibration or displacement/twisting/deformation of the components) of the tomography machine between two acquisition times, a difference value d between the intermediate function values of two acquisition data sets is determined. To achieve robust detection of the misalignment, instead of determining just one single difference value d, a plurality of virtual sectional planes of the body are defined, and for each sectional plane, two intermediate function values are determined on the basis of two acquisition data sets, one value for each set, and one difference value d is in turn determined from these two values. The difference values d are combined to form a total error value D. The number of selected sectional planes may be chosen to be very high in this method, and is limited by the resolution and dimensions of the detector. In addition, the total error value D may be used as the basis for adjusting sequentially one geometry parameter of the tomography machine at a time in order to correct the geometric misalignment. This sequential adjustment may result in a sub-optimum correction result, because not all the geometry parameters are mutually independent. Thus, in some cases, a plurality of iterations may be needed (e.g., repeated optimization of the same geometry parameter).

SUMMARY AND DESCRIPTION

The object is to detect efficiently for acquisition data sets of a tomography machine, a movement made by a body between the acquisition times of the acquisition data sets.

The scope of the present invention is defined solely by the appended claims and is not affected to any degree by the statements within this summary. The present embodiments may obviate one or more of the drawbacks or limitations in the related art.

A method is provided for detecting a movement of at least one part of a body between two acquisition times of at least two acquisition data sets. Each acquisition data set contains pixel values from pixels of a detector surface of a tomography machine, wherein each pixel value characterizes attenuation values of body elements of the body for a projection beam. Each pixel value in particular constitutes what is known as the extinction value ln(IO/I), which is calculated in a manner known in the prior art. In order to detect whether the body or a part thereof has moved between the acquisition times of the acquisition data sets, the acquisition data sets are each compared with one another in pairs. In each paired comparison of a first and of a second of the acquisition data sets, the following acts are performed. For a plurality of virtual sectional planes of the body, a first intermediate function value of the attenuation values of all the body elements lying in the sectional plane is determined on the basis of the first acquisition data set i, and a second intermediate function value of the attenuation values of the sectional plane, (e.g., of all the body elements lying in the sectional plane), is determined on the basis of the second acquisition data set j. This is achieved as follows. Each sectional plane intersects each detector surface at the particular acquisition time along a sectional line. An intermediate function value is assigned to each sectional line. This is done in each case by using the described intermediate function to combine the pixels arranged on the sectional line to form the corresponding intermediate function value.

The intermediate function value for a sectional plane n is denoted here by Sni for the first acquisition data set, and by Snj for the second acquisition data set. For each sectional plane n, a difference value dnij is determined from the first intermediate function value Sni and the second intermediate function value Snj. Thus a total N of sectional planes n produces N difference values dnij, where n is the index value from 1 to N. A total error value $\varepsilon_{ij}$ for the two acquisition data sets is calculated by combining the difference values dnik of all N sectional planes. To avoid having to recalculate the intermediate function values for every comparison of the intermediate function values, all possible intermediate function values may be calculated and saved in the sense of a preprocessing act (e.g., at a predefined scanning rate). The calculation is performed by numerical integration along all possible sectional lines on the detector surface (e.g., 2D Radon transform) and by consecutive numerical differentiation of the line integrals in the direction of their distance parameter (e.g., distance from the coordinate origin in the detector plane).

In order now to define efficiently the in total N sectional planes of the body, those planes that have a common line of intersection are determined as sectional planes. In other words, the sectional planes have a common line of intersection, namely the line connecting the two source positions held by a radiation source of the tomography machine at the two acquisition times. A new sectional plane may thus be generated by rotation about this axis. By virtue of this construction, it is possible to state that pairs of the sectional planes always intersect. In addition, the sectional planes are selected such that at the particular acquisition time, (e.g., within one acquisition data set), the difference between pairs of the sectional lines of the sectional planes is at least one pixel on the detector surface. By virtue of intersecting sectional planes having sectional lines that are spaced apart sufficiently from one another to differ by at least one pixel, it may be provided using little computational effort of a processing unit that translational movements of at least one part of the body along all three spatial axes and also rotational movements about all three spatial axes may be detected reliably. A translational or rotational movement within a single sectional plane does not change in particular the intermediate function value of the associated sectional plane, and hence cannot be detected using the sectional plane alone. By having two intersecting sectional planes, it is impossible for the body to perform a movement for which the intermediate function values of the sectional lines of both sectional planes remain unchanged.

The embodiments also include developments, the features of which result in additional advantages.

One development relates to calculating the total error value $\varepsilon_{ij}$. In this development, for each paired comparison of a first acquisition data set i and of a second acquisition data set j, and for each sectional plane n, the difference value dnij for the intermediate function value Sni of the first acquisition data set i and for the intermediate function value Snj of the second acquisition data set j is calculated as $$dnij=F(|Sni-Snj|)$$

where | | is the absolute value function and F( ) is a compression function, wherein the compression function F has a negative mathematical curvature (second mathematical derivative) for positive values, in particular values greater than 1.

Examples of such functions are:

$$F_1(x)=x^p$$

$$F_2(x)=\tan h(x)$$

where p is a positive number less than 1. It has been found that reliable convergence of an optimization method for motion correction is achieved using this transformed difference value. In particular, it achieves robustness against outliers.

The total error value $\varepsilon_{ij}$ is calculated as:

$$\varepsilon_{ij} = \frac{1}{N}\sum_{n=1}^{N} dnij.$$

The total error value $\varepsilon_{ij}$ thus characterizes for all the sectional planes n, where n=1 . . . N, the difference values dnij. If the body does not move, then |Sni−Snj| is minimal, because now only the effect of other error sources remains (image errors, numerical errors). Any movement of the body between the acquisition times of the first acquisition data set i and the second acquisition data set j produces in at least one of the sectional planes n a change in the intermediate function value in the associated sectional lines of the two acquisition data sets i and j.

One development allows the total error value $\varepsilon_{ij}$ to be used to gain an overview of which acquisition data sets are similar, e.g., differ only slightly as a result of the movement of the body, and which acquisition data sets differ particularly sharply from each other. Thus more than two acquisition data sets are provided in this development. Each paired comparison of every two of these acquisition data sets produces one total error value $\varepsilon_{ij}$. Thus, it is possible to form an error matrix of the paired total error values $\varepsilon_{ij}$ at least between the first acquisition data set i as one half of the pair and each of the rest of the acquisition data sets as the other half of the pair. In other words, the second acquisition data set j is formed for different values of j, wherein j hence represents the index of the different acquisition data sets. The error matrix refers to a data structure for storing the total error values $\varepsilon_{ij}$ for a combination of different acquisition data sets i and j. The error matrix has the advantage that similar body positions may be identified or selected on the basis of total error values.

In order to use this error matrix advantageously, one development provides that an organ moving periodically in the body, (e.g., an organ such as a heart), is imaged by the acquisition data sets from a plurality of projection angles and at different phases of the periodic movement. Since the acquisition data sets image the organ at different phases of the periodic movement, it is not possible to use all the acquisition data sets as the basis for computing a sharp image of the organ as a 3D model. This requires using only those acquisition data sets that image the organ in the same phase of the periodic movement. It is still necessary here, however, to have the organ imaged from different projection angles in order to be able to compute the 3D model at all. The error matrix is accordingly used to determine from the acquisition data sets a consistent subset of the acquisition data sets inside which the acquisition data sets have a lower total error value paired with one another than each acquisition data set of the subset paired with each of the acquisition data sets outside the subset. This determination rule is thus used to determine from the error matrix all those acquisition data sets that represent the organ in the same phase of movement. The acquisition data sets are selected here such that the organ is represented from different projection angles. The subset is then used to reconstruct the graphical 3D model of the organ. This has the advantage that the organ, (e.g., a heart), is imaged sharply or precisely in the 3D model and in this process an image is made for a particular phase of the periodic movement. In the prior art, in order to determine the phase, an electrocardiogram (ECG), for example, was needed to detect the cardiac phases of movement. This has the disadvantage, however, that for irregular cardiac activity, it is difficult to associate the ECG with the acquisition data sets. This is avoided here by forming the subset, because this embodiment does not depend on a measured cardiac activity.

The error matrix may also be used to correct the movement in the acquisition data sets. In this development, a first of the acquisition data sets is geometrically registered with the rest of the acquisition data sets on the basis of parameter data for a translation and/or a rotation of the body. Geometric registration of this type is known per se from the prior art. It requires as parameter data the position of the body and the position of the radiation source and of the detector surface of the tomography machine. It is possible to determine from this data a spatial arrangement of the tomography machine relative to the body and thereby determine corresponding pixels of two acquisition data sets. If, however, the body moves between the acquisition times of the acquisition data sets, then a motion correction ΔP for the body position P is needed. Registration is the determination of this motion correction ΔP. The parameter data for the motion correction ΔP is changed iteratively here by the paired comparison being repeated in each iteration until a combination of the total error values of the error matrix satisfies a predefined optimization criterion. The combination of the total error values constitutes a redundancy measure or consistency measure. The optimization criterion may state, for example, that the combination of the total error values is less than a predefined threshold value. The advantage achieved by the development is that the motion correction ΔP is performed not just between the first acquisition data set i and a single second acquisition data set j, but the acquisition data set i is compared with a plurality of "second" acquisition data sets.

According to a development, a simplex algorithm for changing the parameter data collectively is used in order to determine the parameter data for the motion correction ΔP. This has the advantage that all the parameter data, (e.g., the change in the translation in a plurality of directions and in the rotation about a plurality of spatial axes), may be performed in a single iterative correction process. Thus, unlike in the prior art, there is no need to successively adjust each element of the parameter data.

One development uses the above-defined summation to calculate the total error values of the error matrix. According to an alternative development, the combination of the total error values is calculated as a transform of the intermediate function values. This has the advantage of not needing to calculate the differences between the intermediate function values $S_{ni}$ and $S_{nj}$. Calculating such differences makes the total error value sensitive to outliers.

One development uses the registration of acquisition data sets in conjunction with an angiogram. In this development, in the first acquisition data set, the body is imaged before a contrast agent infusion, and in the rest of the acquisition data sets, the body is imaged during the contrast agent infusion. The first acquisition data set is registered with the rest of the acquisition data sets in the manner described, and after the registration, is used in each case for subtracting tissue information. This produces a corresponding image of a contrast agent material or of a contrast agent bolus of the contrast agent. Hence, a 3D model of the contrast agent bolus alone without the surrounding body tissue may be generated on the basis of the subtraction images. By determining 3D models for a plurality of phases, it is also possible to provide a graphical animation, e.g., a 4D representation.

According to one development, a project data set is extrapolated on the basis of the total error value. This development assumes that in the first acquisition data set, the body is imaged only incompletely, and an extrapolation unit fills in pixel values for a missing part of the body. An extrapolation unit of this type is known per se from the prior art. It may be a program module, for instance. Imaging part of the body, or rather part of the body being missing, may be caused by the image of the body extending beyond the edge of the detector surface. In order to fill in the missing pixel values, it may be assumed, for example, that the body is shaped as an ellipse and it is thereby possible to complete the shape of the truncated part. The problem now is that the inside of the body shape, for instance, also needs filling with detail on whether the missing part of the body is, e.g., fatty tissue or muscle tissue or bone. To do this, the extrapolation unit may extrapolate the edge of the image in the direction of the missing part. In this process, parameters are set, such as, for example, parameters for the fat proportion and for the proportion of muscle tissue. At least one of such parameters of the extrapolation unit is adjusted such that a combination of the total error values of the error matrix satisfies a predefined optimization criterion. In particular, the combination of the total error values is minimized. The combination of the total error values may be formed, for example, using the sum of the total error values. This again produces a consistency measure. The development has the advantage that the extrapolation unit may be operated not solely on the basis of model assumptions for the missing part of the body (for instance ellipse shape), but also on the basis of the specific pixel values of the rest of the acquisition data sets. This results in a more accurate reconstruction of the missing part and fewer artifacts at the edge of the region that is not truncated.

One development of the method facilitates detecting in an acquisition data set an error region, as is produced, for example, when an interfering object, (e.g., a tube or a connector), is arranged between the radiation source and detector surface of the tomography machine. This may be the case only for some of the projection angles if the tube or a connector is dangling from the tomography machine, for instance. By this development, it is possible to locate such an error region, which extends only across a subarea of the detector surface, in at least one acquisition data set by determining, for a particular paired comparison of this acquisition data set with at least one other of the acquisition data sets, not simply just the total error value but a percentage of the total error value c taken by at least one difference value $dn_{ij}$ of the intermediate function values. Thus, the effect of the individual sectional lines on the total error value c is determined. A location of the error region on the detector surface is determined on the basis of the percentage of the total error value $\varepsilon_{ij}$ that is taken by the difference value $dn_{ij}$ formed for a sectional line. A sectional line that crosses the error region produces a larger difference value than a sectional line running outside the error region. The position of the error region on the detector surface may hence be determined.

According to one development, a detector response function is determined. The detector response function characterizes an association of the radiation intensity at a pixel with the pixel value formed therefrom. The detector response function may be a linear function of the intensity. In this development, a calibration phantom is imaged by each of the acquisition data sets. In other words, the acquisition data sets are generated while a calibration phantom is in the tomography machine. By adjusting a compensation function for the detector response function of the pixel sensors of the detector surface, the total error values of all paired comparisons of the acquisition data sets are adjusted such that a predefined optimization criterion for the response function is satisfied. The optimization criterion may state, for example, that the detector response function followed by the compensation function shall produce a linear function.

The described tomography machine has a projection unit for generating an acquisition data set of a body at a definable acquisition time and for a definable projection angle in each case. The tomography machine includes a processing unit, which is designed to perform an embodiment of the method. This has the advantage that it is possible to state for the acquisition data sets whether the body has moved between the acquisition times. The processing unit may be provided on the basis of at least one microprocessor. Graphical processing units (GPUs) are particularly suitable.

According to one development of the tomography machine, the projection unit includes a C-arm having a flat-panel detector, which forms the detector surface. The projection unit may be embodied as an X-ray C-arm for example. In particular, the tomography machine may have a mobile design, so for instance may be wheeled and therefore may also be used in an operating theater.

BRIEF DESCRIPTION OF THE DRAWINGS

FIG. 3 depicts a sketch illustrating an error matrix according to an embodiment. Functionally identical parts are denoted by the same reference signs in each of the figures.

DETAILED DESCRIPTION

Figure 1:
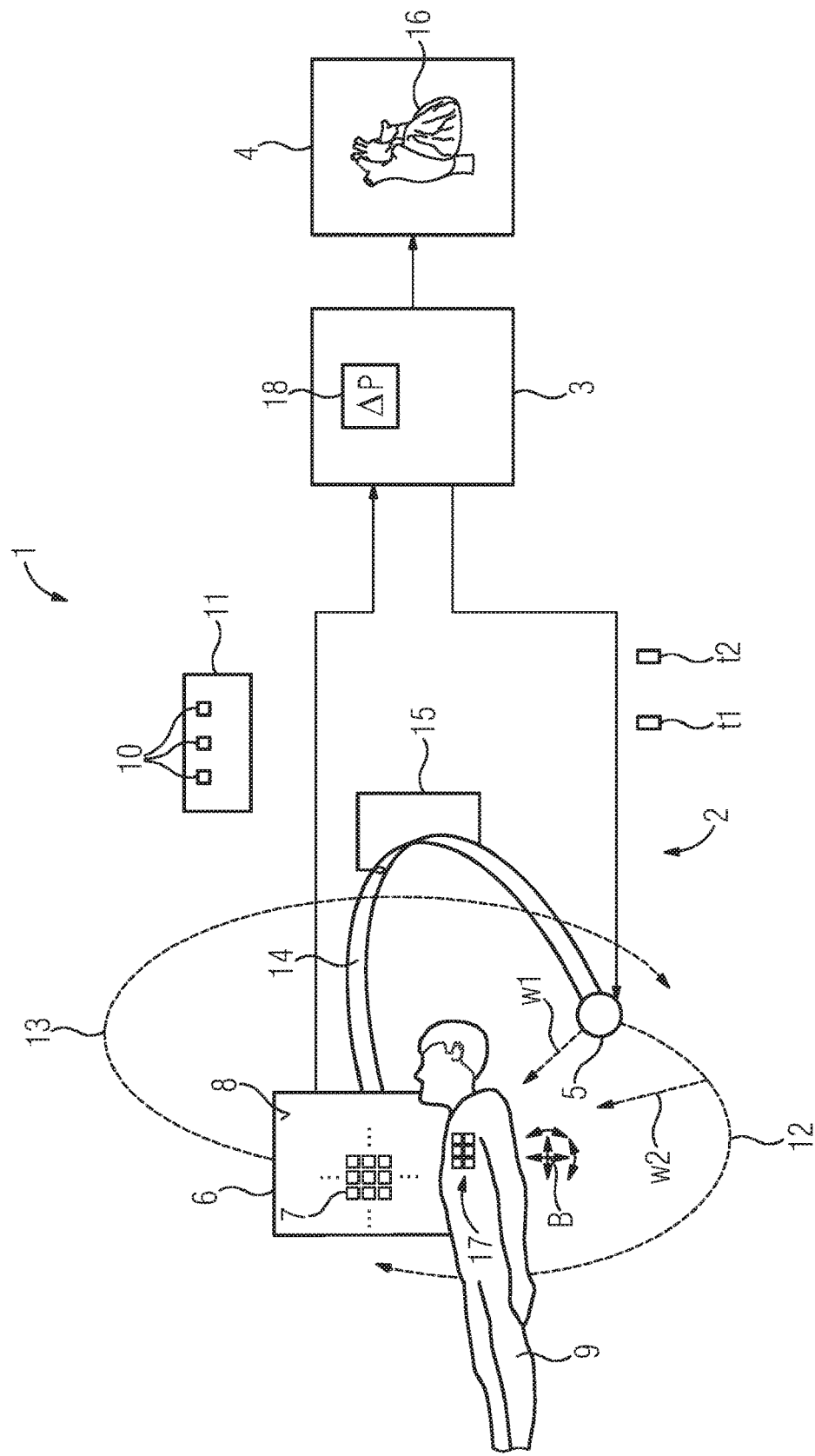
FIG. 1 depicts a schematic diagram of an embodiment of the tomography machine.

FIG. 1 depicts a tomography machine 1. The tomography machine 1 is embodied in particular as a computed tomography machine. The tomography machine 1 may be an X-ray C-arm machine, for instance. The figure depicts a projection unit 2 and a processing unit 3 and a display unit 4. The projection unit 2 may include a radiation source 5 and a detector 6 for the radiation source 5. The radiation source 5 may be, for example, an X-ray radiation source or positron radiation source. The detector unit 6 may be embodied as a flat-panel detector, for instance. The detector may include pixel sensors 7 for detecting the radiation. The pixel sensors 7 as a whole form a detector surface 8, on which is received the radiation from the radiation source 5. The radiation source 5 may be activated at a particular acquisition time t1, t2 by the processing unit 3. It then sends radiation through a body 9, e.g., a patient or a sample of material. The pixel sensors 7 each include a pixel value 10. The pixel values 10 for the particular acquisition time t1, t2 are brought together in a corresponding acquisition data set 11, which may be transferred to the processing unit 3. The acquisition times t1, t2 depicted are merely by way of example. More than the two acquisition times shown may be provided, such as, for example, 100 acquisition times.

Between the acquisition times t1, t2, the radiation source 5 and the detector 6 may be moved along a corresponding path of motion or trajectory 12, 13 around the body 9, (e.g., by a C-arm 14 and a drive unit 15), with the result that at the acquisition times t1, t2, the source 5 sends radiation through the body 9 from a different projection angle w1, w2 at each time. One of the acquisition data sets 11 is then obtained at each projection angle w1, w2.

The processing unit 3 may use all the acquisition data sets 11 to compute a 3D model 16 and may display the 3D model 16 on the display unit 4. The display unit 4 may be a screen, for instance. The 3D model 16 may image or represent, for example, an organ of the body 9, (e.g., an organ such as a heart). Tomograms or sectional images of the body 9 may also be computed instead of the 3D model 16. In order to compute the artificial sectional images or the 3D model 16 from the acquisition data sets 11, it is necessary to calculate from the pixel values 10 for each of the body elements 17, for instance using the back projection method, the attenuation property or absorption property exhibited by the body elements 17 for the radiation from the radiation source 5. The processing unit 7 may represent the body elements 17 by individual volume elements or voxels for short, for example.

To do this requires a precise location of the individual body elements 7 with respect to the radiation source 5 and the detector 6 at each acquisition time t1, t2. If the body 9 or the body elements 7 move by a movement B between the acquisition times t1, t2, the assumption about the location of the body elements 17 no longer holds. The movement B may be a translation and/or a rotation. To correct for the movement B, the processing unit 3 may determine for each acquisition data set 11, parameter data 18 for a motion compensation or motion correction ΔP.

The processing unit 3 may determine from the acquisition data sets 11 whether the body 9 or a part of the body 9, (e.g., an internal organ, has moved by the movement B between the acquisition times t1, t2. The processing unit 3 may be in the form of a personal computer, for instance, for this purpose.

In addition, the parameter data of the motion correction ΔP may be used to correct the change in the pixel arrangement caused by the movement B. For this purpose, the parameter data 18 is modified iteratively on the basis of an optimization criterion and using the simplex method, for instance, and then the parameter data 18 is used as the basis for correcting the movement for an acquisition data set 11, and the corrected acquisition data set is compared with the remaining acquisition data sets.

For an iterative optimization to be possible for the optimization criterion, an error measure is needed, which for the tomography machine 1 is based on calculating intermediate function values. This is illustrated below with reference to FIG. 2.

Figure 2:
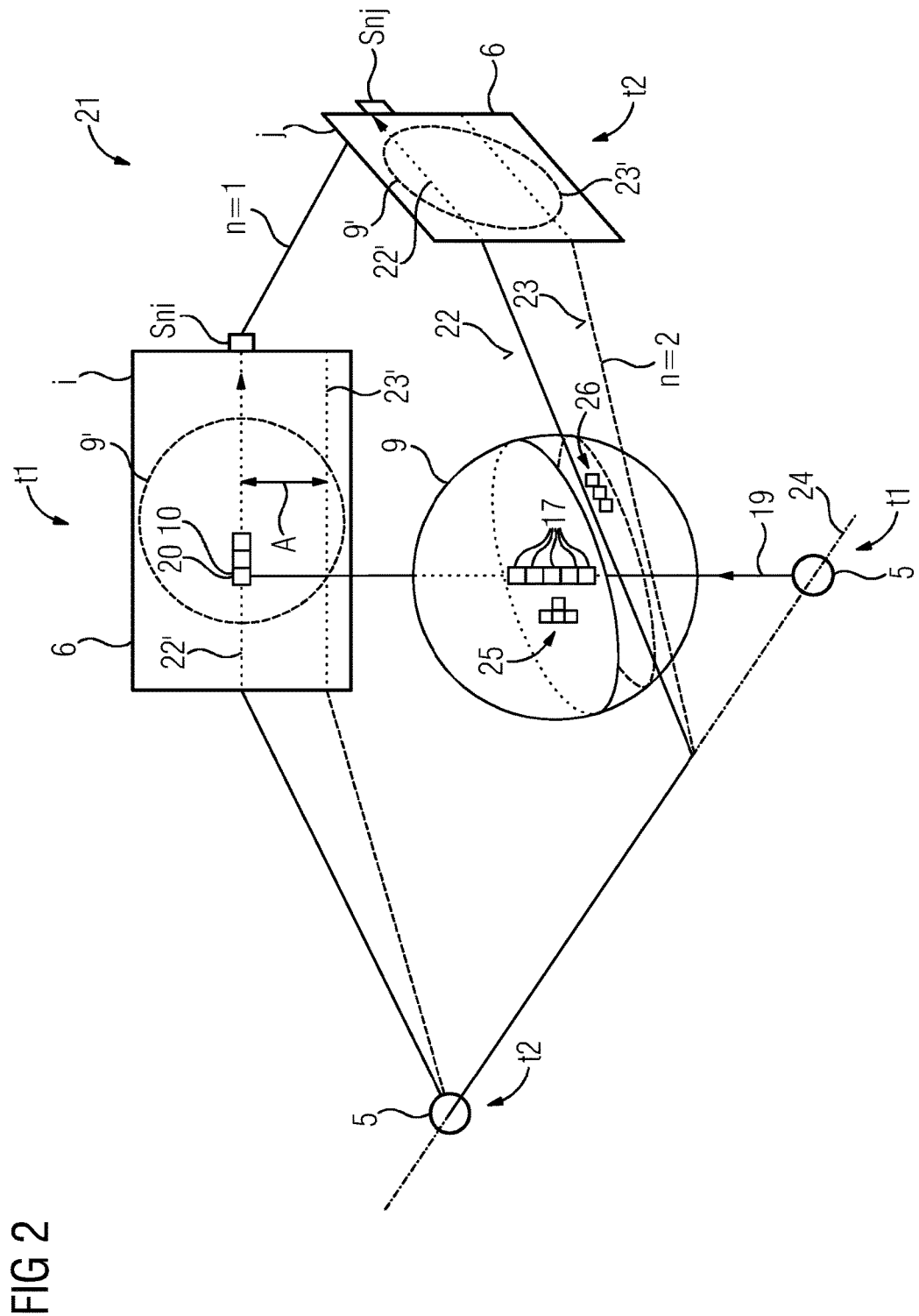
FIG. 2 depicts a sketch illustrating the calculation of intermediate function values according to an embodiment.

FIG. 2 depicts by way of example the position of the radiation source 5 and of the detector 6 for each of the two acquisition times t1, t2. The body 9 is represented by a sphere. The figure indicates a corresponding image 9' of the body 9 on the detector surface 8. It illustrates by way of example how a ray 19 of a radiation beam from the radiation source 5 passes through individual body elements 17 of the body 9. Then it hits a pixel 20, e.g., a single pixel-value sensor 7. A pixel value 10 is determined for the pixel 20. The pixel value 10 reflects the effect of the particular attenuation value exhibited by each body element 17.

FIG. 2 also illustrates the principle of a paired comparison 21 between two acquisition data sets 11, with reference being made here to an acquisition data set i at acquisition time t1 and to an acquisition data set j at acquisition time t2 for the sake of clarity. A plurality of sectional planes 22, 23 of the body 9 are defined for the paired comparison 21. N sectional planes may be defined, which may then have an index n, which is illustrated in FIG. 2 by the index n=1 and n=2 for the two sectional planes 22, 23. N may equal between 500 and 12000, for example. The sectional planes 22, 23 intersect at an axis 24, about which a prototypical sectional plane may be rotated, for instance, in order to define the sectional planes 22, 23. The sectional plane 22 intersects the detector 6 at the respective acquisition times t1, t2 along sectional lines 22' in each case, the sectional plane 23 does it along the sectional lines 23'. A separation A of the sectional lines 22', 23' at each acquisition time t1, t2 is selected such that the sectional lines 22', 23' intersect at least one or more different pixels. The sectional lines 22', 23' thereby differ by at least one pixel 20 for each acquisition time t1, t2.

The pixel values 10 of all the pixels 20 on one of the sectional lines 22', 23' of an acquisition data set i, j may be combined using an intermediate function to form an intermediate function value Sni, Snj, as is known from the prior art. Each intermediate function value Sni, Snj represents in this case the totality 25, 26 of all the body elements 17 that lie within the corresponding sectional plane 22, 23. Therefore the same intermediate function value Sni is obtained for all the sectional lines 22' of the same sectional plane 22. If this is not the case then the same body elements 17 do not lie in the sectional plane 22 at the two acquisition times t1, t2. The same applies to the intermediate function values Snj of all the sectional lines Snj.

Now in order to combine the intermediate function values Sni, Snj for a paired comparison 21 of two acquisition data sets i, j for all the N sectional planes 22, 23, the processing unit 3 may compute the following total error value $\varepsilon_{ij}$:

$$\varepsilon_{ij} = \frac{1}{N} \sum_{n=1}^{N} |Sni - Snj|^P.$$

The value p may be selected here to be less than 1, for example p=0.3. It is also possible, however, for p to have the value 2, for instance, resulting in the squared error. The latter proves to be less robust in optimization, however, because the error is dominated by particularly high intermediate function values (in particular outliers). A different compression function may also be used instead of the compression function F1 given here by way of example.

Performing the paired comparison 21 for every available acquisition data set 11 produces an error matrix 27, as depicted by way of example in FIG. 3. If it is now required, for example, to determine for a first acquisition data set i the similarity with all the rest of the acquisition data sets, then the following consistency value $E_i$ may be calculated for this purpose:

$$E_i = \sum_{i \neq j} \varepsilon_{ij}$$

The consistency value $E_i$ constitutes a combination of the total error values $\varepsilon_{ij}$.

Similarly, it is also possible to calculate for a subset T, which is defined by a plurality of indices i, a consistency measure with respect to the rest of the acquisition data sets:

$$E_T = \sum_{i \in T} \sum_{j \notin T} \varepsilon_{ij}.$$

If it is now required, for example, to optimize the parameter data 18, then the motion correction may be defined as follows:

$$\Delta P = \begin{bmatrix} \alpha \\ \tau \end{bmatrix},$$

where $\alpha=[\alpha 1, \alpha 2, \alpha 3]$ describes a rotation of the body about an axis $\alpha$, and $\tau=[\tau 1, \tau 2, \tau 3]$ a translational movement along a spatial direction $\tau$. $\alpha$ and $\tau$ constitute parameter data of the motion correction $\Delta P$. If $\Delta P$ is now determined and is used to correct the movement in the first acquisition data set i, it is then possible to recalculate a value for the consistency measure $E_i$ and to check whether the consistency measure has improved, e.g., the value $E_i$ has been reduced. The described simplex method may be used for this purpose for simultaneous optimization of $\alpha$ and $\tau$.

The processing unit 3 may also use the consistency measures $E_i$ or $E_T$ to implement further applications.

One application relates to cardiac computed tomography (CT). Four-dimensional (4D) cardiac CTs and 4D C-Arm CT acquisition protocols may be ECG-triggered. In these processes, the ECG is used to define time windows or gates or measurement gates for individual phases of movement of the cardiac cycle. For each gate, a complete acquisition data set that images the heart from a plurality of projection angles w1, w2 is required in order to compute the 3D model 16 or a tomogram. Methods known per se may hence be used to reconstruct the 3D model 16. In place of or in addition to the gates, the intermediate function values Sni, Snj, for instance in the form of the consistency measures $E_i$, $E_T$, may be used to identify the optimum gates, for example to identify their position in time and their time length, in which acquisition data sets 11 are particularly consistent. The gates may thus be placed such that there is the minimum possible cardiac movement within the gate. For example, for generating a subset of the individual gates, successive acquisition data sets having the lowest consistency measure may be added for the projection angles that are still missing. Consistent data may thereby be generated even for irregular cardiac activities that produce an irregular ECG from which it is not possible to define a gate, or only possible unreliably. The method also allows the superimposed respiratory movement to be taken into account, because the choice of the gate is optimized with respect to the overall movement.

In an extension to the described motion correction, it is also possible to use a motion correction for subtraction angiography and perfusion measurements, because in these processes there are a plurality of C-arm rotations about the body 9 in order to obtain a first acquisition data set as a mask or mask scan and then further scans for additional acquisition data sets following injection of a contrast agent. One scan is one cycle of the projection unit, in which the trajectories 12, 13 are traveled. This takes a relatively large amount of time, during which it is likely that a patient moves his body 9. The redundancy measure, in the form of the intermediate function values Sni, Snj, is therefore applied globally to different cycles or scans.

A correction to the acquisition geometry, (e.g., to the geometry of the projection unit 2), on the basis of the intermediate function values Sni, Snj may also be used for software calibration of the tomography machine 1. Particularly in the case of the C-arm, this allows correction of the geometric deformation of the C-arm during variation of the projection angle b1, b2. In addition, alternative trajectories 12, 13 that differ from a circular path are possible for a C-arm, for which trajectories conventional offline calibration techniques fall short. Furthermore, the intermediate function values may be used to determine the consistency of acquisition data sets 11 more robustly because these values may use the full redundancy contained in the acquisition data sets 11.

The redundancy measure, in the form of the intermediate function values Sni, Snj, may also be used for correcting beam hardening effects. The redundancy measure may be used to optimize parameters of the model employed for the beam hardening correction because a more accurate beam hardening correction may result in a reduction in the consistency measure.

Using the redundancy measure, in the form of the intermediate function values Sni, Snj, may also be applied to corrections for scattered radiation through optimization of the convolution kernels used for the scattered radiation estimates, because an acquisition data set that does not contain scattered radiation has a lower consistency measure with respect to the remaining acquisition data sets than an acquisition data set containing scattered radiation. The specific procedure may estimate the convolution kernel, then use this kernel for deconvolution of an acquisition data set and then calculate the consistency measure. By varying the convolution kernel, it is thereby possible to minimize the consistency measure and optimize the scattered radiation estimate.

It is also possible to use the consistency measure $E_i$, $E_T$ to achieve a consistent extrapolation of truncated projections (e.g., truncation correction) because the inconsistency is increased by truncation. In this process, information about truncated projections, (e.g., missing parts of the images 9' of the body 9), is determined from redundant projection data (e.g., projections from directions that contain the truncated region). In particular, optimization of extrapolation data or extrapolation functions is possible here. Parameters, for instance the width and/or the decay properties, may be set for extrapolation functions. Such parameters may then be optimized by minimizing the redundancy measure $E_i$, $E_T$.

Intermediate function values Sni, Snj may also be used for locating image errors. By the geometrical analysis of the individual sectional lines 22', 23' through different detector planes having common redundant sectional planes 22, 23, it is possible to ascertain an increased inconsistency in the individual sectional lines 22', 23' and infer therefrom the location of image errors, e.g., image errors may be located and optionally corrected. For this purpose, points of intersection of the sectional lines that have a particularly high difference value dnij may be analyzed. Image errors may in particular be artifacts or objects that may change over time in the image region, for instance catheters, devices and/or metals.

The redundancy measure may also be used to correct the detector response function.

Since the processing unit 3 in particular may perform the described corrections while the tomography machine 1 is in use, the tomography machine 1 is also suitable as a mobile machine, which may be wheeled into an operating theater, for instance, and may be used there temporarily for an operation. The method may be used to compensate and/or correct for the mobile and hence less stable construction of the tomography machine 1.

To summarize, the example illustrates how a redundancy measure may be used to analyze the consistency of projection data for improving clinical applications of 3D CT (e.g., 3D reconstruction) and 4D CT (e.g., 3D CT with animation in time) and flat-panel detector CT (FDCT).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for detecting a movement of at least one part of a body between acquisition times of at least two acquisition data sets, wherein in a particular paired comparison of a first acquisition data set and a second acquisition data set, the method comprises:

generating, by a projection unit of a tomography machine, the acquisition data sets of the body at the acquisition times;

determining, by a microprocessor of the tomography machine, for a plurality of virtual sectional planes of the body, each virtual sectional plane of which intersects the detector surface at a particular acquisition time along a sectional line, (1) a first intermediate function value of attenuation values of all body elements lying in the sectional plane based on the first acquisition data set, and (2) a second intermediate function value of the attenuation values based on the second acquisition data set;

determining, by the microprocessor, for each sectional plane, a difference value from the first and second intermediate function values;

calculating, by the microprocessor, a total error value for the first and second acquisition data sets by combining the difference values of all the sectional planes;

forming an error matrix of paired total error values between the first acquisition data and the second acquisition data set;

determine, from the error matrix, a subset inside which the acquisition data sets have a lower total error value paired with one another than each acquisition data set of the subset paired with each of the acquisition data sets outside the subset; and compute a three-dimensional model of the at least one part of the body from the determined subset; and display the three-dimensional model on a display unit, wherein, for each paired comparison, the virtual sectional planes have a common line of intersection, and wherein, for the particular acquisition time, the difference between pairs of the sectional lines is at least one pixel, wherein, for each paired comparison and for each sectional plane n, a difference value dnij for an intermediate function value Sni of a first acquisition data set i and for an intermediate function value Snj of a second acquisition data set j is calculated as:

$$dnij = F(|Sni - Snj|)$$

where | | is the absolute value function and F( ) is a predetermined compression function, wherein the compression function F has a negative mathematical curvature at least for values greater than 1, and the total error value $\varepsilon_{ij}$ is calculated as:

$$\varepsilon_{ij} = \frac{1}{N}\sum_{n=1}^{N} dnij.$$

2. The method of claim 1, wherein the at least two acquisition data sets comprise more than two acquisition data sets, and
wherein the error matrix is formed of paired total error values at least between the first acquisition data set as one half of the pair and each of the rest of the acquisition data sets as the other half of the pair.

3. The method of claim 1, wherein a calibration phantom is imaged by each acquisition data set, and by adjusting a compensation function for a detector response function of pixel sensors of the detector surface, the total error values of the paired comparisons of the acquisition data sets are adjusted such that a predefined optimization criterion for the detector response function is satisfied.

4. A method for detecting a movement of at least one part of a body between acquisition times of more than two acquisition data sets, wherein in a particular paired comparison of a first acquisition data set and a second acquisition data set, the method comprises:

generating, by a projection unit of a tomography machine, the acquisition data sets of the body at the acquisition times;

determining, by a microprocessor of the tomography machine, for a plurality of virtual sectional planes of the body, each virtual sectional plane of which intersects the detector surface at a particular acquisition time along a sectional line, (1) a first intermediate function value of attenuation values of all body elements lying in the sectional plane based on the first acquisition data set, and (2) a second intermediate function value of the attenuation values based on the second acquisition data set;

determining, by the microprocessor, for each sectional plane, a difference value from the first and second intermediate function values; and calculating, by the microprocessor, a total error value for the first and second acquisition data sets by combining the difference values of all the sectional planes, wherein, for each paired comparison, the virtual sectional planes have a common line of intersection, wherein, for the particular acquisition time, the difference between pairs of the sectional lines is at least one pixel, wherein an error matrix is formed of paired total error values at least between the first acquisition data set as one half of the pair and each of the rest of the acquisition data sets as the other half of the pair, wherein an organ moving periodically in the body is imaged by the acquisition data sets from a plurality of projection angles and at different phases of the periodic movement of the organ, wherein the error matrix is used to determine from the acquisition data sets a consistent subset inside which the acquisition data sets have a lower total error value paired with one another than each acquisition data set of the subset paired with each of the acquisition data sets outside the subset, and wherein, in the acquisition data sets of the subset, the organ is represented in a same phase of movement from different projection angles, and the subset is used to form a graphical three-dimensional model of the organ.

5. A method for detecting a movement of at least one part of a body between acquisition times of more than two acquisition data sets, wherein in a particular paired comparison of a first acquisition data set and a second acquisition data set, the method comprises:

generating, by a projection unit of a tomography machine, the acquisition data sets of the body at the acquisition times;

determining, by a microprocessor of the tomography machine, for a plurality of virtual sectional planes of the body, each virtual sectional plane of which intersects the detector surface at a particular acquisition time along a sectional line, (1) a first intermediate function value of attenuation values of all body elements lying in the sectional plane based on the first acquisition data set, and (2) a second intermediate function value of the attenuation values based on the second acquisition data set;

determining, by the microprocessor, for each sectional plane, a difference value from the first and second intermediate function values; and calculating, by the microprocessor, a total error value for the first and second acquisition data sets by combining the difference values of all the sectional planes, wherein, for each paired comparison, the virtual sectional planes have a common line of intersection, wherein, for the particular acquisition time, the difference between pairs of the sectional lines is at least one pixel, wherein an error matrix is formed of paired total error values at least between the first acquisition data set as one half of the pair and each of the rest of the acquisition data sets as the other half of the pair, wherein the first acquisition data set is geometrically registered with the rest of the acquisition data sets based on parameter data for a translation, rotation, or translation and rotation of the body, wherein the parameter data is changed iteratively by the paired comparison being repeated in each iteration until a combination of the total error values of the error matrix satisfies a predefined optimization criterion, wherein the error matrix is used to determine from the acquisition data sets a subset inside which the acquisition data sets have a lower total error value paired with one another than each acquisition data set of the subset paired with each of the acquisition data sets outside the subset, and wherein the subset is used to form and display a graphical three-dimensional model of the at least one part of the body.

6. The method of claim 5, wherein the parameter data is changed collectively using a simplex algorithm.

7. The method of claim 6, wherein the combination of the total error values is calculated as a transform of the intermediate function values.

8. The method of claim 7, wherein, in the first acquisition data set, the body is imaged before a contrast agent infusion,
wherein, in a remainder of the acquisition data sets, the body is imaged during the contrast agent infusion, and
wherein the first acquisition data set is used after the registration to subtract tissue information, whereby a corresponding image of a contrast agent bolus is produced.

9. The method of claim 5, wherein the combination of the total error values is calculated as a transform of the intermediate function values.

10. The method of claim 5, wherein in the first acquisition data set, the body is imaged before a contrast agent infusion,
wherein, in a remainder of the acquisition data sets, the body is imaged during the contrast agent infusion, and
wherein the first acquisition data set is used after the registration to subtract tissue information, whereby a corresponding image of a contrast agent bolus is produced.

11. A method for detecting a movement of at least one part of a body between acquisition times of more than two acquisition data sets, wherein in a particular paired comparison of a first acquisition data set and a second acquisition data set, the method comprises:
generating, by a projection unit of a tomography machine, the acquisition data sets of the body at the acquisition times;
determining, by a microprocessor of the tomography machine, for a plurality of virtual sectional planes of the body, each virtual sectional plane of which intersects the detector surface at a particular acquisition time along a sectional line, (1) a first intermediate function value of attenuation values of all body elements lying in the sectional plane based on the first acquisition data set, and (2) a second intermediate function value of the attenuation values based on the second acquisition data set;
determining, by the microprocessor, for each sectional plane, a difference value from the first and second intermediate function values; and
calculating, by the microprocessor, a total error value for the first and second acquisition data sets by combining the difference values of all the sectional planes,
wherein, for each paired comparison, the virtual sectional planes have a common line of intersection,
wherein, for the particular acquisition time, the difference between pairs of the sectional lines is at least one pixel,
wherein an error matrix is formed of paired total error values at least between the first acquisition data set as one half of the pair and each of the rest of the acquisition data sets as the other half of the pair,
wherein, in the first acquisition data set, the body is incompletely imaged, and an extrapolation unit fills in pixel values for a missing part of the body,
wherein at least one parameter of the extrapolation unit is adjusted such that a combination of the total error values of the error matrix satisfies a predefined optimization criterion,
wherein the error matrix is used to determine from the acquisition data sets a subset inside which the acquisition data sets have a lower total error value paired with one another than each acquisition data set of the subset paired with each of the acquisition data sets outside the subset, and
wherein the subset is used to form and display a graphical three-dimensional model of the at least one part of the body.

12. A method for detecting a movement of at least one part of a body between acquisition times of at least two acquisition data sets, wherein in a particular paired comparison of a first acquisition data set and a second acquisition data set, the method comprises:
generating, by a projection unit of a tomography machine, the acquisition data sets of the body at the acquisition times;
determining, by a microprocessor of the tomography machine, for a plurality of virtual sectional planes of the body, each virtual sectional plane of which intersects the detector surface at a particular acquisition time along a sectional line, (1) a first intermediate function value of attenuation values of all body elements lying in the sectional plane based on the first acquisition data set, and (2) a second intermediate function value of the attenuation values based on the second acquisition data set;
determining, by the microprocessor, for each sectional plane, a difference value from the first and second intermediate function values; and
calculating, by the microprocessor, a total error value for the first and second acquisition data sets by combining the difference values of all the sectional planes,
wherein, for each paired comparison, the virtual sectional planes have a common line of intersection,
wherein, for the particular acquisition time, the difference between pairs of the sectional lines is at least one pixel,
wherein an error region, which extends only across a subarea of the detector surface, is located in at least one acquisition data set in each case by determining, for a particular paired comparison of the at least one acquisition data set with at least one other of the acquisition data sets, a percentage of the total error value taken by at least one difference value, and based on the percentage, determining a location of the error region on the detector surface from the sectional line associated with the difference value,
wherein an error matrix is formed of paired total error values at least between the first acquisition data set and the second acquisition data set,
wherein the error matrix is used to determine from the acquisition data sets a consistent subset inside which the acquisition data sets have a lower total error value paired with one another than each acquisition data set of the subset paired with each of the acquisition data sets outside the subset, and
wherein the subset is used to form and display a graphical three-dimensional model of the at least one part of the body.

13. A tomography machine comprising:
a projection unit configured to generate acquisition data sets of a body at definable acquisition times and for definable projection angles in each case; and
a microprocessor configured to:
determine, for a plurality of virtual sectional planes of the body, each virtual sectional plane of which intersects a detector surface at a particular acquisition time along a sectional line, (1) a first intermediate function value of attenuation values of all body elements lying in the sectional plane based on a first acquisition data set, and (2) a second intermediate function value of the attenuation values based on a second acquisition data set;

determine, for each sectional plane, a difference value from the first and second intermediate function values; and calculate a total error value for the first and second acquisition data sets by combining the difference values of all the sectional planes, wherein, for each paired comparison, the virtual sectional planes have a common line of intersection, wherein, for the particular acquisition time, the difference between pairs of the sectional lines is at least one pixel, wherein, for each paired comparison and for each sectional plane n, a difference value dnij for an intermediate function value Sni of a first acquisition data set i and for an intermediate function value Snj of a second acquisition data set j is calculated as:

$$dnij = F(|Sni - Snj|)$$

where | | is the absolute value function and F( ) is a predetermined compression function, wherein the compression function F has a negative mathematical curvature at least for values greater than 1, and the total error value $\varepsilon_{ij}$ is calculated as:

$$\varepsilon_{ij} = \frac{1}{N} \sum_{n=1}^{N} dnij,$$

wherein an error matrix is formed of paired total error values at least between the first acquisition data set and the second acquisition data set, wherein the error matrix is used to determine from the acquisition data sets a consistent subset inside which the acquisition data sets have a lower total error value paired with one another than each acquisition data set of the subset paired with each of the acquisition data sets outside the subset, and wherein the subset is used to compute a graphical three-dimensional model of the at least one part of the body; and a display unit configured to display the graphical three-dimensional model of the at least one part of the body.

14. The tomography machine of claim 13, wherein the projection unit comprises a C-arm having a flat-panel detector comprising a detector surface.

* * * * *